(12) United States Patent
Lenz (10) Patent No.: US 7,888,006 B2
(45) Date of Patent: Feb. 15, 2011

(54) METHOD FOR ISOLATING DNA FROM BIOLOGICAL SAMPLES

(75) Inventor: Christian Lenz, Dusseldorf (DE)

(73) Assignee: Qiagen GmbH, Hilden (DE)

( * ) Notice: Subject to any disclaimer, the term of this patent is extended or adjusted under 35 U.S.C. 154(b) by 332 days.

(21) Appl. No.: 10/490,810

(22) PCT Filed: Sep. 26, 2002

(86) PCT No.: PCT/EP02/10823

§ 371 (c)(1), (2), (4) Date: Sep. 20, 2004

(87) PCT Pub. No.: WO03/035903

PCT Pub. Date: May 1, 2003

(65) Prior Publication Data

US 2005/0019769 A1 Jan. 27, 2005

(30) Foreign Application Priority Data

Sep. 26, 2001 (DE) ................................ 101 47 439

(51) Int. Cl.
 *C12Q 1/68* (2006.01)
 *C07H 21/02* (2006.01)
 *C07H 21/04* (2006.01)
(52) U.S. Cl. .................... 435/6; 536/22.1; 536/23.1; 536/24.3
(58) Field of Classification Search ............... 536/22.1, 536/23.1, 24.3, 25.4; 435/6
See application file for complete search history.

(56) References Cited

U.S. PATENT DOCUMENTS

| | | | | |
|---|---|---|---|---|
| 5,081,028 A | * | 1/1992 | Hofstetter et al. | 435/6 |
| 5,234,809 A | | 8/1993 | Boom et al. | 435/91 |
| 5,334,501 A | * | 8/1994 | Adams et al. | 435/6 |
| 5,693,785 A | * | 12/1997 | Woodard et al. | 536/25.4 |
| 5,912,148 A | * | 6/1999 | Eggerding | 435/91.2 |
| 5,990,301 A | * | 11/1999 | Colpan et al. | 536/25.4 |
| 6,130,073 A | | 10/2000 | Eggerding | 435/91.2 |
| 6,548,256 B2 | * | 4/2003 | Lienau et al. | 435/6 |
| 6,562,568 B1 | * | 5/2003 | Kleiber et al. | 435/6 |
| 6,699,987 B2 | * | 3/2004 | Hillebrand et al. | 536/25.4 |
| 2001/0051341 A1 | * | 12/2001 | Lo et al. | 435/6 |
| 2003/0152974 A1 | * | 8/2003 | Gauch et al. | 435/6 |
| 2003/0170669 A1 | * | 9/2003 | Garvin | 435/6 |
| 2003/0199078 A1 | * | 10/2003 | Kleiber et al. | 435/270 |
| 2004/0014703 A1 | * | 1/2004 | Hollnder et al. | 514/44 |
| 2006/0073546 A1 | * | 4/2006 | Botstein et al. | 435/69.1 |
| 2006/0185024 A1 | * | 8/2006 | Ivarie et al. | 800/7 |

FOREIGN PATENT DOCUMENTS

EP 0310913 * 9/1988

OTHER PUBLICATIONS

Merel et al., Completely automated extraction of DNA from whole blood. Clinical Chemistry 42(8): 1285-1266 (1996).*
van Bergen et al., Replication of origin containing adenovirus DNA fragments that do not carry the terminal protein. Nucleic Acids Res. 11: 1975-1989 (1983).*
Bowtell et al., Rapid Isolation of DNA. Analytical Biochemistry Analytical Biochemistry 162(2) : 463-464 (1987).*
The Stratagene Catalog p. 39 (1988).*
Kunkel et al. Analysis of human Y-chromosome specific reiterated DNA in chromosome variants. PNAS 74(3) :1245-1249.*
Davis et al. "Basic Methods in Molecular Biology" pp. 44-50. Elsevier Science Publishing Co., Inc. NY, NY (1986).*
Qiagen News Is. 4 : 9-10 (1997). http://www1.qiagen.com/literature/qiagennews/0497/974intro.pdf.*
Hossain et al., Modified guanidinium thiocyanate method for human sperm DNA isolation. Molecular Human Reproduction 3 (11) :953-956 (1997).*
4M Guanidine Hydrochloride applied to the isolation of DNA from different sources. FEB Letters 62(1) : 81-84 (1976).*
Ciulla et al., Analytical Biochemistry, 174:485-488 (1988).
Marko et al., Analytical Biochemistry, 121:382-387 (1982).
Grimberg et al., Nucleic Acids Research, 17(20):8390 (1989).
Lahiri et al., Journal of Biochemical and Biophysical Methods, 25:193-205 (1992).
Miller et al., Nucleic Acids Research, 16(3):1215 (1988).
Parzer et al., Biochem. J., 273:229-231 (1991).
Salazar et al., Clinical Chemistry 44(8):1748-1750 (1998).
Vogelstein et al., Proc. Natl. Acad. Sci. USA, 76(2):615-619 (1979).

* cited by examiner

*Primary Examiner*—Ethan Whisenant
(74) *Attorney, Agent, or Firm*—Thomas A. Haag, Esq.; Fanelli Strain & Haag, PLLC (57) ABSTRACT

The present invention relates to an improved process for isolating DNA from biological samples, particularly from human whole blood.

54 Claims, 3 Drawing Sheets

METHOD FOR ISOLATING DNA FROM BIOLOGICAL SAMPLES

CROSS REFERENCE TO RELATED APPLICATIONS

This application is a United States national phase filing under 35 U.S.C. §371 of international (PCT) application No. PCT/EP02/10823, filed Sep. 26, 2002, designating the United States, which application claims priority to German Patent Appln. No. 101 47 439.3, filed Sep. 26, 2001.

The present invention relates to an improved process for isolating DNA from biological samples, particularly from human whole blood.

The purification of nucleic acids plays a central role in molecular biology. The purified DNA is used among other things as a starting material for diagnosis based on nucleic acids, for establishing genetic profiles and for pharmacogenomics. Therefore, the isolation of nucleic acids such as DNA and RNA from biological samples, such as for example blood, body secretions, tissue samples, urine, stools and the like, for subsequent use in genetic analyses is of particular importance.

In the methods known from the prior art for recovering nucleic acids, DNA is isolated from cells and tissues by lysing the starting materials under highly denaturing and reducing conditions, partly using protein-degrading enzymes, purifying the nucleic acid fractions obtained by means of phenol/chloroform extraction processes and recovering the nucleic acids from the aqueous phase by dialysis or ethanol precipitation [Sambrook, J., Fritsch, E. F. in T. Maniatis, C S H, "Molecular Cloning", 1989].

These long-established methods of isolating DNA from cells and particularly from tissues have serious disadvantages, however: on the one hand they are very time-consuming and require considerable experimental effort. In addition, such procedures are associated with an acute risk of damage to the health of the people carrying out the isolation owing to the chemicals which have to be used, such as chloroform or phenol.

The inevitable consequence of the disadvantages described above was that over time alternative methods would be developed for isolating nucleic acids from different biological starting materials, by which the laborious and health-damaging phenol/chloroform extraction of nucleic acids could be avoided and the time taken should be reduced.

All these proposed methods known from the prior art are based on a method developed and first described by Vogelstein and Gillespie [Proc. Natl. Acad. Sci. USA, 1979, 76, 615-619] for the preparative and analytical purification of DNA fragments from agarose gels. The method combines the dissolving of the agarose containing DNA bands in a chaotropic saline solution with binding of the DNA to carrier particles. The fixed DNA is then washed with a washing solution (20 mM EDTA; 50% v/v ethanol) and then detached from the carrier particles.

Hitherto, this method has undergone a number of modifications and is still used for different processes for extracting and purifying nucleic acids from various sources (Marko, M. A., Chipperfield, R. and Birnboim, H. G., 1982, Anal. Biochem. 121, 382-387).

In addition, worldwide, there are now a number of reagent systems, particularly for purifying DNA fragments from agarose gels and for isolating plasmid DNA from bacterial lysates, but also for isolating longer-chained nucleic acids (genomic DNA, total cell RNA) from blood, tissues or cell cultures.

Many of these commercially available purification systems are based on the reasonably well known principle of binding nucleic acids to mineral carriers in the presence of solutions of different chaotropic salts. In these systems, suspensions of finely ground glass powder, diatomaceous earth or silica gels are used as carrier materials.

A process for isolating nucleic acids which may be implemented for a number of different applications is disclosed in U.S. Pat. No. 5,234,809. This discloses a process for isolating nucleic acids from starting materials which contain nucleic acids by incubating the starting material with a chaotropic buffer and a DNA-binding solid phase. The chaotropic buffers bring about both lysing of the starting material and binding of the nucleic acids to the solid phase. The process is used to isolate nucleic acids from small samples and is particularly used in practice for isolating viral nucleic acids.

The physicochemical principle of the prior-art systems currently used and commercially available for isolating nucleic acids based on the binding of nucleic acids to the surfaces of mineral carriers is supposed to consist of the disruption of the higher structures of the aqueous medium by which the nucleic acids are adsorbed on to the surface of mineral materials, particularly glass or silica particles. The disruption of the higher structures of the aqueous medium is always effected in the presence of chaotropic ions and is virtually quantitative when high concentrations of these ions are present. On the physicochemical basis described above a number of commercially available systems for isolating nucleic acids contain buffer compositions with chaotropic salts having high ionic strength which are regarded as necessary for the binding of nucleic acids to a nucleic acid-binding solid phase.

However, among the serious disadvantages of the process are the fact that the lysing effected by the chaotropic buffers is by no means suitable for all materials or is extremely inefficient for larger quantities of starting materials and is extremely time-consuming. In addition, different concentrations of different chaotropic buffers have to be used for different situations, which proves very complicated.

On the other hand, the isolation of nucleic acids based on a salting out step is known from the prior art [L. A. Salazar et al., Clin. Chem. 44 (1998) 1748; S. A. Miller et al., Nucleic Acid Res., 16(3) (1988) 1215]. These processes has the disadvantage, however, that during the process the reaction vessel has to be changed at least once, with the risk of mixing up the samples. Furthermore, the salted out proteins can only be separated from the nucleic acid which is to be purified by using the experimentally laborious method of centrifugation.

Another process for purifying DNA obtained from blood is disclosed by T. A. Ciulla [Analytical Biochemistry, 174 (1988) 485]. In this, first of all the cell nuclei are liberated by a lysing step. The DNA contained therein is isolated using guanidinium-iso-thiocyanate and β-mercaptoethanol and subsequent precipitation with 2-propanol. However, this process includes relatively time-consuming steps for resuspension and centrifuging. Moreover, this process uses a lysing buffer which is susceptible to microbial growth and has to be used in a nine-fold excess in relation to the blood. Furthermore, β-mercaptoethanol is classed as a toxic substance.

The aim of the present invention is therefore to provide a process which overcomes the disadvantages of the processes known from the prior art.

In particular, the problem of the present invention is to avoid the use of toxic or corrosive substances in the isolation of DNA.

Furthermore, the present invention sets out to propose a less time-consuming and less laborious process for isolating DNA.

A further aim of the present invention is to provide a process which can be carried out without changing the reaction vessel—as a so-called "one-pot reaction"—and thereby minimises the risk of confusion or contamination of the samples.

The above problems are solved according to the invention by mixing the biological sample with a lysing reagent in a reaction vessel. In the next step the cell components which contain DNA are separated from the other cell components. This separation may be done by centrifuging, for example.

The DNA contained in the sediment is then separated from other impurities such as proteins, for example. This separation is achieved by resuspending the sediment in a saline solution. Optionally, the contaminants may also be separated from the DNA by heating and/or by the use of enzymes. The DNA is subsequently precipitated by the addition of alcohol and the precipitate is separated from the solution. This may be done, for example, by centrifuging or by winding the DNA on a glass hook. After washing with a washing fluid in which salts dissolve but not the DNA, followed by drying, the DNA is resuspended in a suitable buffer.

Examples of biological samples containing nucleic acid may be cell-free sample material, plasma, body fluids, such as blood, buffy coat, cells, leukocyte fractions, crusta phlogistica, sputum, urine, sperm or organisms (single- or multi-celled organisms; insects etc) or eukaryotes or prokaryotes.

In particular, blood (human whole blood), buffy coat, leukocyte fractions and cell cultures are suitable for carrying out the process according to the invention.

Blood (human whole blood) is most particularly suitable for carrying out the process according to the invention.

Suitable lysing reagents for carrying out the process according to the invention are the detergent-containing lysing reagents known from the prior art. Large numbers of suitable detergents are known from the prior art.

Lysing reagents which are particularly suitable for solving the problem according to the invention are those which contain detergents selected from among the groups Triton, Tween, NP-40 or mixtures of substances from these groups. Among these groups, the Triton group is particularly suitable, while Triton X-100 (octylphenol polyethoxylate) is particularly preferred.

According to the invention, lysing reagents based on 0.5 to 7.5% by volume of detergent are preferably used, while a content of 1.0 to 5.0% by volume is particularly preferred.

If desired, salts of mono- or divalent cations and complexing agents may be added, individually or in combination, to the lysing reagent.

According to the invention, lysing reagents based on 0.5 to 200 mM of magnesium chloride, 0.5 to 200 mM potassium chloride and 0.5 to 100 mM ethylenediamine tetraacetate and/or ethylenedioxy-bis-(ethylenenitrilo)tetraacetic acid are preferably used.

Most preferably, lysing reagents based on 1 to 30 mM magnesium chloride, 1 to 20 mM potassium chloride and 1 to 10 mM ethylenediamine tetraacetate and/or 1 to 10 mM ethylenedioxy-bi-(ethylenenitrilo)tetraacetic acid are used.

If desired, one or more buffers may be added to the lysing reagent. The pH of the lysing reagent may be varied over a wide range and in order to carry out the process according to the invention is preferably in the range from pH 2 to 10, more preferably in the range from pH 3 to 9. The buffer systems known to the skilled man for adjusting the pH may be used. According to the invention, buffer systems based on tris(hydroxymethyl)aminomethane are preferably used. Most preferably, a buffer system based on 0.5 to 250 mM tris(hydroxymethyl)aminomethane hydrochloride is used.

Most preferably, a lysing buffer is used which contains 13 mM tris(hydroxymethyl)aminomethane hydrochloride, pH 8.0, 10 to 14.5 mM magnesium (II)chloride hexahydrate, 10 mM potassium chloride, 2 to 5 mM ethylenediamine tetraacetate and/or 1 to 2 mM ethylenedioxy-bis(ethylenenitrilo) tetraacetic acid as well as 2% by volume of Triton X-100.

Suitable saline solutions for resuspending the sediment containing the nucleic acid in order to carry out the process according to the invention are the solutions known from the prior art for this purpose, based on high salt concentrations, particularly using chaotropic salts. By chaotropic salts are meant according to the invention salts which have a high affinity for water and therefore form a large hydrate shell; suitable chaotropic salts are known in large numbers from the prior art.

According to the invention, solutions containing urea, guanidinium iso-thiocyanate or guanidinium hydrochloride are preferably used, individually or in combination, the latter being particularly preferred.

In particular, solutions based on 0.5 to 7.0M guanidinium hydrochloride are preferably used to solve the problems according to the invention.

Solutions based on 2.0 to 4.0M guanidinium hydrochloride are most preferably used.

Denaturing solutions of this kind may optionally contain other substances such as complexing agents or buffers. The pH of the denaturing buffer may vary over a wide range in order to carry out the process according to the invention; it preferably has a pH in the range from 3 to 10 and most preferably in the range from 7.5 to 9.5. The buffer systems known to the skilled man may be used to adjust the pH. According to the invention, buffer systems based on tris(hydroxymethyl)aminomethane are preferably used. Most preferably, a buffer system based on 0.5 to 250 mM of tris(hydroxymethyl)aminomethane hydrochloride is used.

Most preferably, a denaturing buffer containing 3 M guanidinium hydrochloride and 50 mM tris(hydroxymethyl)aminomethane hydrochloride, pH 8.5, is used.

In order to assist the denaturing activity of the denaturing buffer the sample may optionally be heated. The reaction temperature of this optional step of the process according to the invention is within the range from 15 to 95° C., preferably in the range from 30 to 85° C. and this step is particularly preferably carried out at a temperature of 65° C.

In order to further separate the DNA from impurities the sample may optionally be treated with enzymes. The process according to the invention may conveniently be carried out using proteases, lipases, amylases and other breakdown enzymes known in the art or mixtures thereof.

The DNA may expediently be precipitated in order to carry out the process according to the invention by means of alcohols known from the prior art such as straight-chain or branched $C_1$-$C_4$ alkanols. Propan-2-ol (iso-propanol) and ethanol have proved particularly suitable.

The washing fluid used is, in particular, a mixture of a straight-chain or branched $C_1$-$C_4$ alkanol with water, while aqueous solutions of ethanol are particularly preferred. A 70% by volume solution of ethanol in water is particularly preferred.

Suitable "low salt solutions" for resuspending the DNA precipitates include all liquids capable of dissolving DNA. Solutions or suitable buffers are also known in large numbers from the prior art.

According to the invention, low salt solutions (solutions with a low ion strength) are preferred, this category including water, according to the invention.

Such solutions may optionally contain other substances such as complexing agents or buffers. The pH of the buffer may vary over a wide range and is preferably in the range pH 6 to 10 and more preferably in the range pH 7.5 to 9.5. The buffer systems known to the skilled person in the art may be used to adjust the pH. According to the invention, buffers based on tris(hydroxymethyl)aminomethane are preferably used. A buffer system based on 0.5 to 150 mM tris(hydroxymethyl)aminomethane hydrochloride is particularly preferred.

Most particularly preferred as a hydrogenation buffer is a solution containing 10 mM tris(hydroxymethyl)aminomethane hydrochloride, pH 8.5.

The Examples that follow are intended to illustrate the present invention:

EXAMPLE 1

DNA Isolation from Human Whole Blood

Human whole blood is pipetted into a reaction vessel containing 2.5 volumes of lysing buffer (13 mM Tris-Cl; 10 mM KCl; 14.5 mM $MgCl_2 \times 6H_2O$; 2 mM EDTA; 2.0% Triton X-100; pH 8). After inverting 5 times, the lysate is centrifuged off, thus sedimenting DNA-containing cell components such as cell nuclei and mitochondria. The supernatant is discarded. Then the sediment is homogenised in denaturing buffer (3 M guanidinium HCl; 50 mM Tris-Cl pH 8.5) by vortexing or pipetting up and down. Proteins are eliminated by QIAGEN Protease in a 10 min incubation at 65° C. The DNA is precipitated from this solution by the addition of 1 volume of isopropanol and centrifugation. After the supernatant has been decanted off, the DNA pellet is washed with 70% ethanol, centrifuged again, the supernatant is removed completely, the DNA is dried and resuspended in a low salt buffer or water.

The following Table 1 shows the results from 6 DNA purifications carried out in parallel, in each case from 3 ml human whole blood which has been anticoagulated with potassium-EDTA:

TABLE 1

| Prep.-No. | Yield [µg] | A260/A280 |
|---|---|---|
| 1 | 62 | 1.84 |
| 2 | 76 | 1.92 |
| 3 | 67 | 1.94 |
| 4 | 68 | 1.93 |
| 5 | 66 | 1.92 |
| 6 | 58 | 1.95 |

The average yield of the 6 extractions is 66 µg, corresponding to 98% of the yield to be expected theoretically from the leukocyte cell count. The coefficient of variation is 8%.

Figure 1:
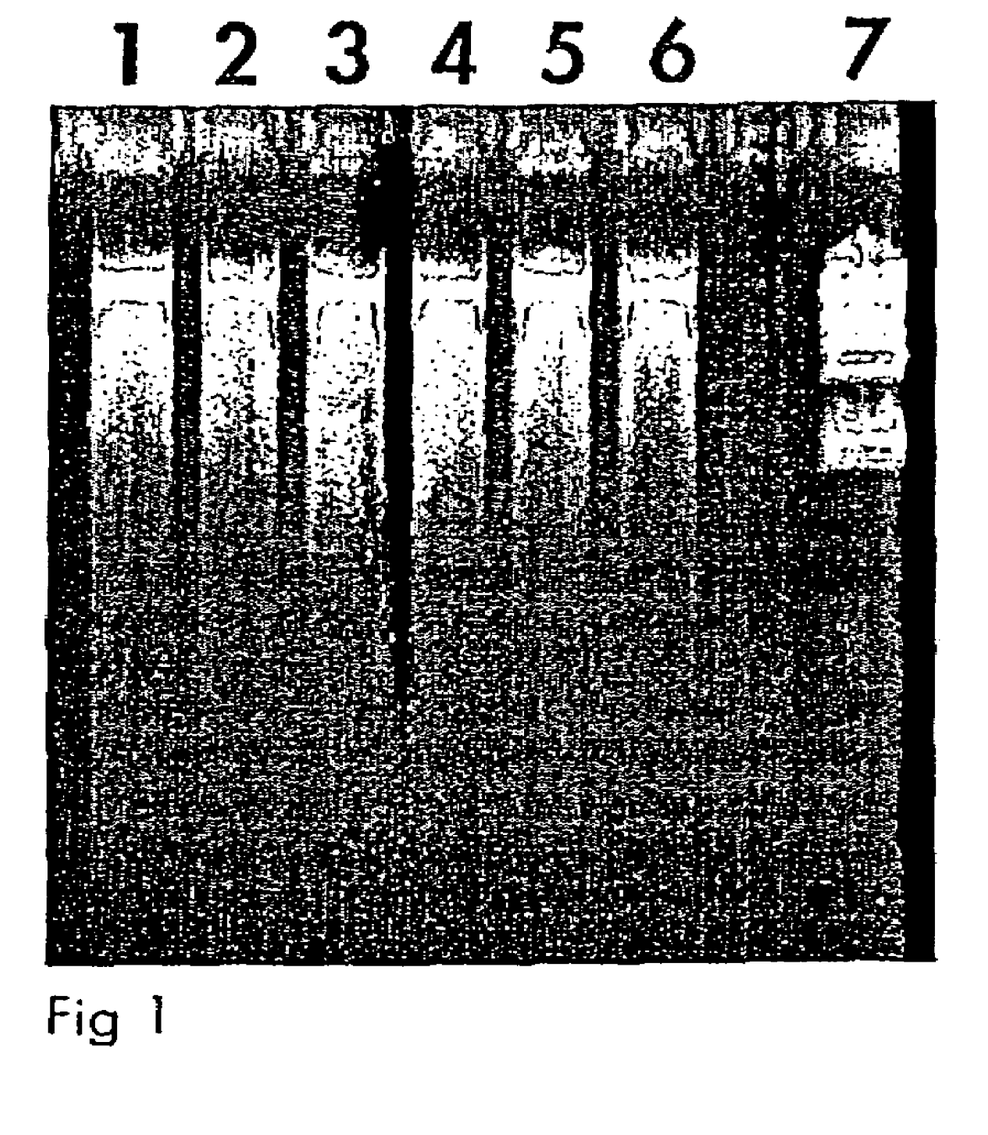
FIG. 1 shows the electrophoretic analysis of a DNA isolated from human whole blood according to Example 1.

In FIG. 1 in each case 2 µl of the DNA solutions obtained are applied to a 0.8% agarose gel.

Figure 2:
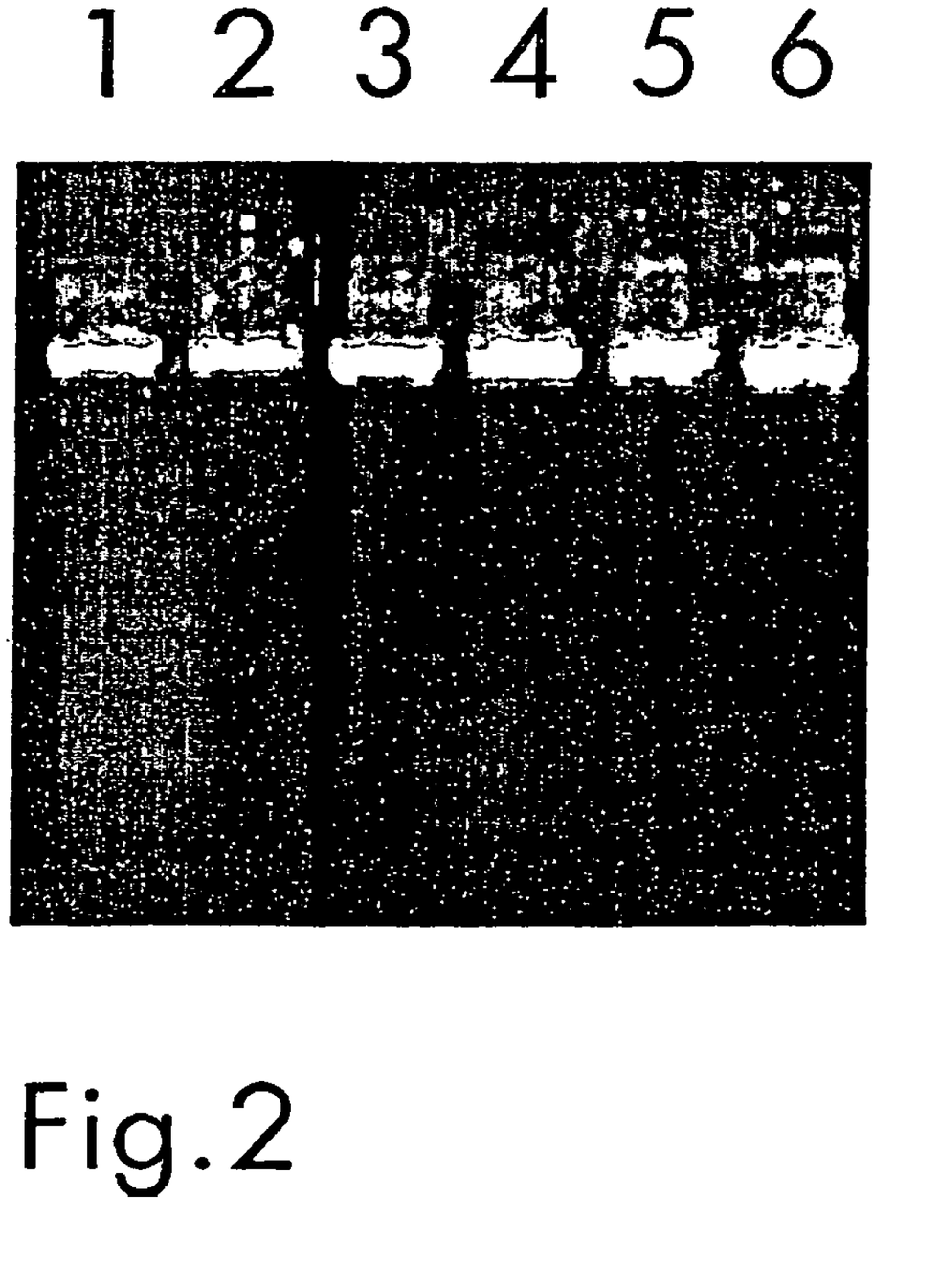
FIG. 2 shows the electrophoretic analysis of a polymerase chain reaction (PCR) with the aim of amplifying a single-copy gene (human analog of giant larvae gene)

FIG. 2 shows the electrophoretic analysis of a polymerase chain reaction (PCR) with the aim of amplifying a single copy gene (human analog of giant larvae gene) using purified genomic DNA as matrix. The experiment shows that all six extractions yield pure DNA which can be amplified without any problems.

EXAMPLE 2

DNA Isolation from Buffy Coat

The purification of DNA from Buffy Coat is carried out using the same method as described in Example 1 for whole blood. Unlike in the whole blood procedure [sic]

Table 2 shows the results of 3×6 purifications carried out in parallel with increasing amounts (200; 300; 500 µl) of Buffy Coat:

TABLE 2

| Vol. Buffy Coat | Prep.-No. | Yield [µg] | A260/A280 | Average Yield [µg] | Coeff. var. [%] |
|---|---|---|---|---|---|
| 200 µl | 1 | 47 | 1.80 | | |
| | 2 | 52 | 1.82 | | |
| | 3 | 50 | 1.80 | | |
| | 4 | 51 | 1.83 | | |
| | 5 | 53 | 1.81 | | |
| | 6 | 49 | 1.83 | 50 | 4 |
| 300 µl | 7 | 74 | 1.83 | | |
| | 8 | 75 | 1.84 | | |
| | 9 | 71 | 1.85 | | |
| | 10 | 75 | 1.84 | | |
| | 11 | 73 | 1.83 | | |
| | 12 | 70 | 1.85 | 73 | 3 |
| 500 µl | 13 | 125 | 1.83 | | |
| | 14 | 111 | 1.85 | | |
| | 15 | 118 | 1.84 | | |
| | 16 | 122 | 1.83 | | |
| | 17 | 118 | 1.84 | | |
| | 18 | 122 | 1.86 | 119 | 4 |

The experiment shows that the yield increases in linear manner in relation to the starting volume of Buffy Coat.

EXAMPLE 3

DNA Isolation from Cell Culture Cells

The purification of DNA from cell culture cells (HeLa cell line) was carried out using the same method as described in Example 1 for whole blood.

Table 3 shows the results from 8 DNA purifications carried out in parallel, in each case from $1 \times 10^6$ cells per 200 µl PBS:

TABLE 3

| Prep.-No. | Yield [µg] | A260/A280 |
|---|---|---|
| 1 | 21 | 1.91 |
| 2 | 20 | 1.91 |
| 3 | 20 | 1.92 |
| 4 | 21 | 1.93 |
| 5 | 19 | 1.94 |
| 6 | 19 | 1.94 |
| 7 | 18 | 1.93 |
| 8 | 19 | 1.95 |

The average yield of the 8 extractions is 20 µg. The coefficient of variation is 6%.

Figure 3:
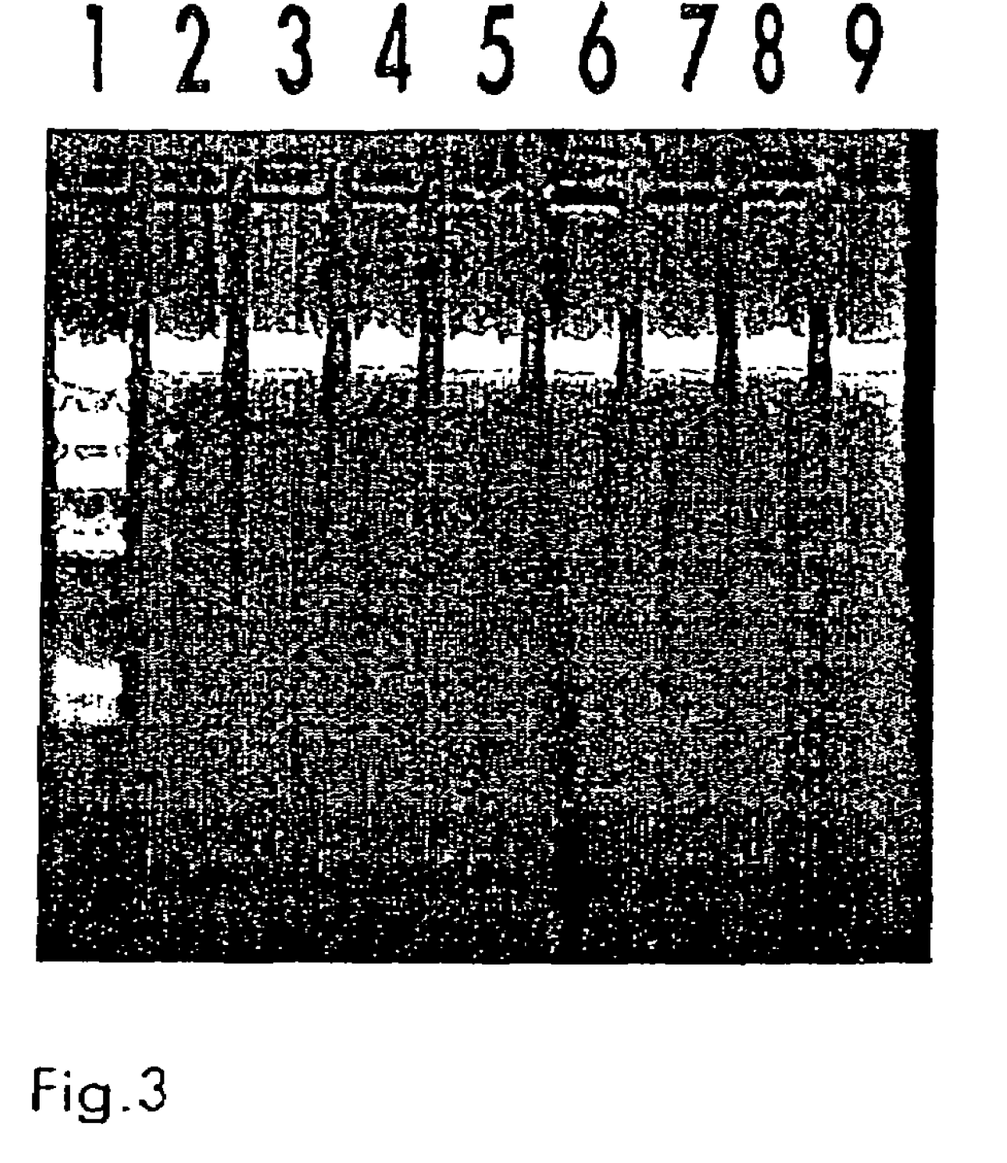
FIG. 3 shows the electrophoretic analysis of a DNA isolated from a cell culture according to Example 3

In FIG. 3 in each case 15 μl of the DNA solutions obtained were applied to a 0.8% agarose gel.

EXAMPLE 4

DNA Isolation from Human Whole Blood with Various Modifications to the Procedure The purification of DNA was carried out as described in Example 1. In one alternative form of the procedure no QIAGEN Protease is added. In a second alternative form of the procedure again no QIAGEN Protease is added and furthermore the incubation at 65° C. is omitted. All the other steps of the 3 variants are identical.

Table 4 summarises the results of this experiment:

TABLE 4

| blood volume | yield [%] | yield CV [%] | 260/280 | 220/260 | hugl PCR [%] |
|---|---|---|---|---|---|
| +Protease/+65° C. | | | | | |
| ≦500 μl | 104 | 3 | 1.84 | 0.79 | 93 |
| ≦3 ml | 93 | 10 | 1.87 | 0.73 | 98 |
| ≦10 ml | 94 | 8 | 1.85 | 0.71 | 98 |
| Average | 97 | 7 | 1.85 | 0.75 | 97 |
| −Protease/+65° C. | | | | | |
| ≦500 μl | 94 | 5 | 1.84 | 0.78 | 98 |
| ≦3 ml | 86 | 12 | 1.86 | 0.75 | 94 |
| ≦10 ml | 84 | 11 | 1.86 | 0.75 | 95 |
| Average | 88 | 9 | 1.85 | 0.76 | 96 |
| −Protease/−65° C. | | | | | |
| ≦500 μl | 94 | 7 | 1.85 | 0.83 | 90 |
| ≦3 ml | 74 | 14 | 1.78 | 0.90 | 100 |
| ≦10 ml | 85 | 10 | 1.85 | 0.78 | 100 |
| Average | 84 | 10 | 1.83 | 0.84 | 97 |

All three alternative methods yield DNA of comparable purity and amplifiability.

EXAMPLE 5

Use of Lysing Reagents with Various Salts:

Genomic DNA is purified from human whole blood according to Example 1. To lyse the blood, lysing buffer with different salts are used. The following Table summarises the alternative lysing buffers used with the corresponding relative yields:

TABLE 5

| Buffer | Yield [%] |
|---|---|
| 13 mM Tris-Cl; 10 mM KCl; 14.5 mM MgCl$_2$; 2 mM EDTA; 2% Triton X-100; pH 8 | 100 |
| 20 mM Tris-Cl; 10 mM KCl; 5/10 mM MgCl$_2$; 2 mM EDTA; 2% Triton X-100 | 105/96 |
| 20 mM Tris-Cl; 10 mM KCl; 14.5 mM MgCl$_2$; 10/20/50 mM (NH$_4$)$_2$SO$_4$; 2 mM EDTA; 2% Triton X-100 | 108/103/103 |
| 20 mM Tris-Cl; 10 mM KCl; 15 mM MgCl$_2$; 150/200/250 mM (NH$_4$)$_2$SO$_4$; 2 mM EDTA; 2% Triton X-100 | 102/93/97 |
| 20 mM Tris-Cl; 10 mM KCl; 1/2.5 mM ZnCl$_2$; 2 mM EDTA; 2% Triton X-100 | 108/88 |
| 20 mM Tris-Cl; 10 mM KCl; 1/2.5/3/4/5 mM ZnCl$_2$; 5 mM MgCl$_2$; 2 mM EDTA; 2% Triton X-100 | 91/94/96/100/99 |
| 20 mM Tris-Cl; 10 mM KCl; 15 mM CaCl$_2$; 2 mM EDTA; 2% Triton X-100 | 111 |
| 20 mM Tris-Cl; 10 mM KCl; 10 mM CaCl$_2$; 2 mM MgCl$_2$; 2 mM EDTA; 2% Triton X-100 | 104 |

EXAMPLE 6

Use of Lysing Reagents with Different Buffer Substances/pH Values:

Genomic DNA is purified from human whole blood according to Example 1. To lyse the blood, lysing buffer with different buffer substances/pH values are used. The following Table summarises the alternative lysing buffers used with the corresponding relative yields:

TABLE 6

| buffer | Yield [%] |
|---|---|
| 13 mM Tris-Cl pH 8.0; 10 mM KCl; 14.5 mM MgCl$_2$; 2 mM EDTA; 2% Triton X-100 | 100 |
| 50/100 mM Na-acetate pH 4.0; 10 mM KCl; 15 mM MgCl$_2$; 2 mM EDTA; 2% Triton X-100 | 107/110 |
| 50/100 mM glycine-HCl pH 3.0; 10 mM KCl; 15 mM MgCl$_2$; 2 mM EDTA; 2% Triton X-100 | 99/106 |
| 50/100/160 mM lysine-HCl pH 3.0/3.3/3.4; 10 mM KCl; 15 mM MgCl$_2$; 4 mM EGTA; 2% Triton X-100 | 103/107/124 |
| 50/100/160 mM lysine-HCl pH 3.3/3.5/3.7; 10 mM KCl; 15 mM MgCl$_2$; 2 mM EGTA; 2% Triton X-100 | 109/101/100 |
| 50/100/160 mM lysine-HCl pH 4.3/4.7/4.6; 10 mM KCl; 15 mM MgCl$_2$; 2% Triton X-100 | 109/116/113 |
| 50 mM ornithine-HCl pH 3.0; 10 mM KCl; 14.5 mM MgCl$_2$; 2 mM EGTA; 2% Triton X-100 | 111 |

EXAMPLE 7

Use of Lysing Reagents with Different Complexing Agents:

Genomic DNA is purified from human whole blood according to Example 1. To lyse the blood, lysing buffers are used with different complexing agents. The following Table summarises the alternative lysing buffers used with the corresponding relative yields (EGTA=ethylenedioxy-bis-(ethylenenitrilo)-tetra-acetic acid; DTPA=diethylenetriamine-penta-acetic acid):

TABLE 7

| Buffer | Yield [%] |
|---|---|
| 13 mM Tris-Cl pH 8.0; 10 mM KCl; 14.5 mM MgCl$_2$; 2 mM EDTA; 2% Triton X-100 | 100 |
| 13 mM Tris-Cl pH 8.0; 10 mM KCl; 14.5 mM MgCl$_2$; 3/4/4.5/5 mM EDTA; 2% Triton X-100 | 97/113/101/103 |
| 13 mM Tris-Cl pH 8.0; 10 mM KCl; 14.5 mM MgCl$_2$; 1 mM EGTA; 2% Triton X-100 | 124 |
| 13 mM Tris-Cl pH 8.0; 10 mM KCl; 14.5 mM MgCl$_2$; 2 mM EDTA; 1 mM EGTA; 2% Triton X-100 | 106 |
| 13 mM Tris-Cl pH 8.0; 10 mM KCl; 14.5 mM MgCl$_2$; 1/2 mM DTPA; 2% Triton X-100 | 101/99 |
| 13 mM Tris-Cl pH 8.0; 10 mM KCl; 14.5 mM MgCl$_2$; 1/2 mM DTPA; 2 mM EDTA; 2% Triton X-100 | 95/102 |
| 13 mM Tris-Cl pH 8.0; 10 mM KCl; 14.5 mM MgCl$_2$; 1/2 mM Na$_5$P$_3$O$_{10}$; 2% Triton X-100 | 79/197 |

TABLE 7-continued

| Buffer | Yield [%] |
| --- | --- |
| 13 mM Tris-Cl pH 8.0; 10 mM KCl; 14.5 mM MgCl$_2$; 1/2 mM Na$_5$P$_3$O$_{10}$; 2 mM EDTA; 2% Triton X-100 | 95/92 |
| 20 mM Tris-Cl pH 8.0; 10 mM KCl; 15 mM MgCl$_2$; 1/2 mM EGTA; 1% Triton X-100 | 110/102 |
| 20 mM Tris-Cl pH 8.0; 10 mM KCl; 15 mM MgCl$_2$; 2/4 mM EGTA; 2% Triton X-100 | 111/140 |

EXAMPLE 8

Use of Lysing Reagents with Different Detergent Concentrations:

Genomic DNA is purified from human whole blood according to Example 1. To lyse the blood, lysing buffers are used with different detergent concentrations. The following Table summarises the alternative lysing buffers used with the corresponding relative yields:

TABLE 8

| Buffer | Yield [%] |
| --- | --- |
| 13 mM Tris-Cl pH 8.0; 10 mM KCl; 14.5 mM MgCl$_2$; 2 mM EDTA; 1/2/2.5/3/4% Triton X-100 | 103/100/103/102/98 |

EXAMPLE 9

Use of Saline Solutions for Resuspending the Material Containing DNA with Different Buffer Substances/pH Values:

Genomic DNA is purified from human whole blood according to Example 1. The lysing reagent used is 13 mM Tris-Cl pH 8.0; 10 mM KCl; 14.5 mM MgCl$_2$; 1 mM EGTA; 2% Triton X-100. To resuspend the material containing DNA saline solutions are used with different buffer substances/pH values. The following Table summarises the alternatives used with the corresponding relative yields:

TABLE 9

| Buffer | Yield [%] |
| --- | --- |
| 3 M guanidinium hydrochloride; 50 mM Tris-Cl pH 8.5 | 100 |
| 3 M guanidinium hydrochloride; 5 mM CaCl$_2$; 50 mM Tris-Cl pH 8.5 | 118 |
| 3 M guanidinium hydrochloride; 5 mM CaCl$_2$; 50 mM Tris pH 9.5 | 129 |
| 3 M guanidinium hydrochloride; 50 mM glycine-NaOH pH 10.0 | 124 |
| 3 M guanidinium hydrochloride; 5 mM CaCl$_2$; 50 mM glycine-NaOH pH 10.0 | 124 |

EXAMPLE 10

Use of Saline Solutions for Resuspending the Material Containing DNA with Different Chaotropic Salts:

Genomic DNA is purified from human whole blood according to Example 1. The lysing reagent used is 13 mM Tris-Cl pH 8.0; 10 mM KCl; 14.5 mM MgCl$_2$; 1 mM EGTA; 2% Triton X-100. To resuspend the material containing DNA saline solutions are used with different chaotropes. The following Table summarises the alternatives used with the corresponding relative yields:

TABLE 10

| Buffer | Yield [%] |
| --- | --- |
| 3 M guanidinium hydrochloride; 50 mM Tris-Cl pH 8.5 | 100 |
| 3 M guanidinium hydrochloride; 0.1 M urea; 50 mM Tris-Cl pH 8.5 | 100 |
| 2.5 M guanidinium hydrochloride; 0.5 M urea; 50 mM Tris-Cl pH 8.5 | 98 |
| 2 M guanidinium hydrochloride; 1 M urea; 50 mM Tris-Cl pH 8.5 | 94 |
| 1.5 M guanidinium hydrochloride; 1.5 M urea; 50 mM Tris-Cl pH 8.5 | 101 |
| 1.5 M urea; 50 mM Tris-Cl pH 8.5 | 86 |

EXAMPLE 11

Different Temperatures During the Protease Incubation

Genomic DNA is purified from human whole blood according to Example 1. The lysing reagent used is 13 mM Tris-Cl pH 8.0; 10 mM KCl; 14.5 mM MgCl$_2$; 1 mM EGTA; 2% Triton X-100. The incubation with protease was carried out for 5 or 10 min at different temperatures. The following Table summarises the results:

TABLE 11

| Incubation | Yield [%] |
| --- | --- |
| 5 min 65° C. | 100 |
| 10 min 65° C. | 99 |
| 5 min 75° C. | 95 |
| 10 min 75° C. | 85 |
| 5 min 85° C. | 84 |
| 10 min 85° C. | 70 |

EXAMPLE 12

Lipase Incubation

Genomic DNA is purified from human whole blood according to Example 1. The lysing reagent used is a) 13 mM Tris-Cl pH 8.0; 10 mM KCl; 14.5 mM MgCl$_2$; 2 mM EDTA; 1 mM EGTA; 2% Triton X-100 or b) 13 mM Tris-Cl pH 8.0; 10 mM KCl; 14.5 mM MgCl$_2$; 2 mM EDTA; 2% Triton X-100. Variants with and without lipase incubation (5 min at 60° C.) before the protease incubation are compared:

TABLE 12

| Incubation | Yield [%] |
| --- | --- |
| a) −Lipase | 100 |
| a) +Lipase | 93 |
| b) −Lipase | 100 |
| b) +Lipase | 91 |

The invention claimed is:
1. A process for isolating DNA from a biological sample, comprising
   (a) mixing a biological sample with a lysing reagent,
   (b) separating the DNA-containing cell components from the other cell components in the mixture,
   (c) resuspending the DNA-containing cell components in a saline solution which contains a chaotropic salt,

(d) removing contaminating ingredients from the resulting suspension by chemical, thermal and/or enzymatic treatment,
(e) precipitating the DNA and retaining the precipitate,
(f) washing the DNA precipitate,
(g) retaining and drying the washed DNA, and
(h) optionally resuspending the DNA in a low salt solution, wherein the isolation process is carried out in one reaction vessel and wherein the lysing reagent comprises, at least one salt of a mono- or divalent cation and one or more complexing agents; wherein the lysing reagent is not susceptible to microbial growth.

2. The process according to claim 1, wherein a detergent-containing lysing reagent is used as the lysing reagent.

3. The process according to claim 2, wherein the detergent is selected from the group consisting of Triton, Tween, or NP-40, or mixtures thereof.

4. The process according to claim 2, wherein the detergent is Triton X-100.

5. The process according to claim 2, wherein the lysing reagent contains 0.5 to 7.5% by volume of detergent.

6. The process according to claim 1, wherein the lysing reagent may additionally contain one or more buffer substances.

7. The process according to claim 6, wherein the buffer substance is selected from the group consisting of tris(hydroxymethyl)aminomethane-hydrochloride, sodium acetate, glycine-hydrochloride, lysine-hydrochloride and ornithine-hydrochloride.

8. The process according to claim 6, wherein the pH of the lysing reagent is in the range from 2 to 10.

9. The process according to claim 6, wherein the lysing reagent contains 13 mM Tris(hydroxymethyl)aminomethane hydrochloride, pH 8.0, 10 to 14.5 mM magnesium(II)chloride hexahydrate, 10 mM potassium chloride, 2 to 5 mM ethylenediaminetetraacetate and/or 1 to 2 mM ethylenedioxy-bis(ethylenenitrilo)tetra-acetic acid and 2% by volume of Triton X-100 in aqueous solution.

10. The process according to claim 1, wherein the saline solution for resuspending the DNA-containing material contains at least guanidinium hydrochloride as a chaotropic salt and may optionally contain urea and/or guanidinium-iso-thiocyanate as chaotropic salts.

11. The process according to claim 1, wherein the saline solution for resuspending the DNA-containing material is an aqueous, 0.5 to 7.0 M guanidinium hydrochloride solution, which may optionally contain as further auxiliaries, buffer substances, detergents or complexing agents.

12. The process according to claim 11, wherein the saline solution for resuspending the DNA-containing material is an aqueous, 2.0 to 4.0 M guanidinium hydrochloride solution, which may optionally contain further auxiliaries such as buffer substances, detergents or complexing agents.

13. The process according to claim 11, wherein the saline solution contains a buffer system based on tris(hydroxymethyl)aminomethane or glycine-sodium hydroxide.

14. The process according to claim 11, wherein the pH of the buffered saline solution is in a range from 3 to 10.

15. The process according to claim 11, wherein the saline solution for resuspending the DNA-containing material comprises an aqueous 3 M guanidinium hydrochloride solution and 50 mM Tris(hydroxymethyl)aminomethane hydrochloride, pH 8.5.

16. The process according to claim 1, wherein the removing contaminating ingredients comprises heating the sample to a temperature in a range from 15° C. to 95° C.

17. The process according to claim 1, wherein the removing contaminating ingredients comprises treating with enzymes to break down contaminants.

18. The process according to claim 1, wherein the nucleic acid is precipitated by the addition of a branched or unbranched $C_1$-$C_4$-alkanol, or mixtures of these alcohols.

19. The process according to claim 1, wherein the washing in step (f) is performed by a solution comprising a mixture of a branched or unbranched $C_1$-$C_4$-alkanol and water.

20. The process according to claim 1 wherein the low salt solution comprises a solvent or a saline solution in which the DNA dissolves.

21. The process according to claim 20, wherein water is used as solvent.

22. The process according to claim 20, wherein the saline solution or the solvent contains a buffer based on tris(hydroxymethyl)aminomethane and/or optionally complexing agents.

23. The process according to claim 22, wherein the pH of the low salt solution is in the range from 6 to 10.

24. The process according to claim 23, wherein an aqueous solution of 10 mM tris(hydroxymethyl)aminomethane-hydrochloride with a pH of 8.5 is used as the low salt solution.

25. The process according to claim 1, wherein human whole blood is used as the biological sample.

26. The process according to claim 1, wherein buffy coat is used as the biological sample.

27. The process according to claim 1, wherein a cell culture is used as the biological sample.

28. A kit for performing the process of claim 1, said kit comprising the following aqueous solutions:
(a) a detergent;
(b) at least one salt of a mono- or divalent cation and one or more complexing agents;
(c) optionally a buffer system comprising tris(hydroxymethyl)aminomethane-hydrochloride, sodium acetate, glycine-hydrochloride, lysine-hydrochloride or ornithine-hydrochloride;
(d) a salt solution for resuspending the DNA-containing material said solution comprising chaotropic salts comprising at least guanidinium hydrochloride which may optionally be used in admixture with urea and/or guanidinium-iso-thiocyanate;
(e) enzymes for breaking down impurities;
(f) a branched or unbranched $C_1$-$C_4$ alcohol, or mixtures of these alcohols for precipitating the nucleic acids;
(g) optionally a washing liquid consisting of a mixture of a branched or unbranched $C_1$-$C_4$-alkanol and water;
(h) a low salt solution or a solvent in which the nucleic acids dissolve, as well as optionally buffers based on tris(hydroxymethyl)aminomethane and/or optionally complexing agents; and
(i) optionally other auxiliaries for carrying out the process according to claim 1.

29. The process according to claim 2, wherein the lysing reagent comprises 1.0% to 5.0% by volume of detergent.

30. The process according to claim 1, wherein the at least one salt of a mono- or divalent cation comprises 1 mM to 30 mM magnesium chloride and/or 1 mM to 20 mM potassium chloride and the complexing agent comprises 1 mM to 10 mM ethylenediaminetetraacetate and/or 1 mM to 10 mM ethylenedioxy-bis(ethylenenitrilo)tetra-acetic acid.

31. The process according to claim 7, wherein the buffer substance is from about 0.5 mM to about 250 mM.

32. The process according to claim 6, wherein the lysing reagent is from pH 3 to pH 9.

33. The process according to claim 13, wherein the buffer system comprises 0.5 mM to 250 mM tris(hydroxymethyl) aminomethane hydrochloride.

34. The process according to claim 11, wherein the saline solution is from pH 7.5 to pH 9.5.

35. The process according to claim 1, wherein the removing contaminating ingredients comprises heating to about 30° C. to about 85° C.

36. The process according to claim 17, wherein said enzymes for breaking down contaminants are selected from the group consisting of proteases, lipases, amylases, or mixtures thereof.

37. The process according to claim 18, wherein the nucleic acid is precipitated by the addition of propan-2-ol(iso-propanol).

38. The process according to claim 19, wherein said mixture is comprised of a solution of ethanol in water.

39. The process according to claim 38, wherein said mixture is comprised of 70% by volume ethanol in water.

40. The process according to claim 22, wherein said buffer is 150 mM tris(hydroxymethyl)aminomethane hydrochloride.

41. The process according to claim 22, wherein the low salt buffer is from about pH 7.5 to about 9.5.

42. The kit according to claim 28, wherein said at least one salt of a mono- or divalent cation comprises 0.5 mM to 200 mM magnesium(II)chloride and/or 0.5 mM to 200 mM potassium chloride and said complexing agent comprises 0.5 mM to 100 mM ethylenediamine tetraacetate and/or 0.5 mM to 100 mM ethylenedioxy-bis(ethylenenitrilo)tetraacetic acid.

43. The kit according to claim 28, wherein said at least one salt of a mono- or divalent cation comprises 1 mM to 30 mM magnesium chloride and/or 1 mM to 20 mM potassium chloride and said complexing agent comprises 1 mM to 10 mM ethylenediamine tetraacetate and/or 1 mM to 10 mM ethylenedioxy-bis-(ethylenenitrilo)-tetra-acetic acid.

44. The kit according to claim 28, wherein said buffer system is from about 0.5 mM to 250 mM.

45. The kit according to claim 28, wherein said enzymes for breaking down contaminants are selected from the group consisting of proteases, lipases, amylases, or mixtures thereof.

46. The kit according to claim 28, wherein said $C_1$-$C_4$ alcohol is propan-2-ol(iso-propanol).

47. The kit according to claim 28, wherein said washing liquid is comprised of a solution of ethanol in water.

48. The kit according to claim 47, wherein said solution is comprised of 70% ethanol by volume in water.

49. The kit according to claim 28, wherein said buffer is 150 mM tris(hydroxymethyl)aminomethane hydrochloride.

50. The process according to claim 1, wherein the at least one salt of a mono- or divalent cation comprises 0.5 mM to 200 mM magnesium chloride and/or 0.5 mM to 200 mM potassium chloride and said complexing agent comprises 0.5 mM to 100 mM ethylenediamine tetraacetate.

51. The process according to claim 1 wherein step (d) does not involve centrifugation.

52. The process according to claim 1 wherein step (d) involves thermal treatment.

53. The process according to claim 1 wherein step (d) involves chemical treatment.

54. The process according to claim 1 wherein step (d) involves enzymatic treatment.

\* \* \* \* \*